United States Patent [19]

Hogan

[11] Patent Number: 4,869,719
[45] Date of Patent: Sep. 26, 1989

[54] ANCHORING MECHANISM FOR AN ADJUSTABLE LENGTH PERCUTANEOUS DRAINAGE CATHETER

[75] Inventor: J. Martin Hogan, Long Beach, Calif.

[73] Assignee: City of Hope, Duarte, Calif.

[21] Appl. No.: 298,874

[22] Filed: Jan. 18, 1989

Related U.S. Application Data

[63] Continuation of Ser. No. 920,422, Oct. 20, 1986, abandoned.

[51] Int. Cl.4 .............................................. A61M 25/02
[52] U.S. Cl. .................................... 604/174; 604/178; 128/DIG. 26
[58] Field of Search .............................. 128/DIG. 26; 604/174–180

[56] References Cited

U.S. PATENT DOCUMENTS

| | | | |
|---|---|---|---|
| 1,032,611 | 7/1912 | Keyes | 604/178 |
| 1,696,763 | 12/1928 | Hare | 604/179 |
| 2,649,092 | 8/1953 | Wallace | 604/105 |
| 3,444,861 | 5/1969 | Schulte | 128/DIG. 26 |
| 3,769,975 | 11/1973 | Nimoy et al. | 604/177 X |
| 4,022,191 | 5/1977 | Jamshidi | 604/263 X |
| 4,419,094 | 12/1983 | Patel | 604/174 X |
| 4,516,968 | 5/1985 | Marshall et al. | 604/174 |
| 4,579,120 | 4/1986 | MacGregor | 604/180 X |
| 4,645,492 | 2/1987 | Weeks | 604/174 |
| 4,650,473 | 3/1987 | Bartholomew et al. | 604/174 |

Primary Examiner—Dalton L. Truluck
Attorney, Agent, or Firm—Edward S. Irons

[57] ABSTRACT

A catheter apparatus having a catheter tube with a length adjusting mechanism positioned on the catheter tube which can be used to change the length of the catheter tube from a bushing which is used to retain the catheter adjacent the patient's skin to the end of the catheter tube that is inserted in the patient.

13 Claims, 4 Drawing Sheets

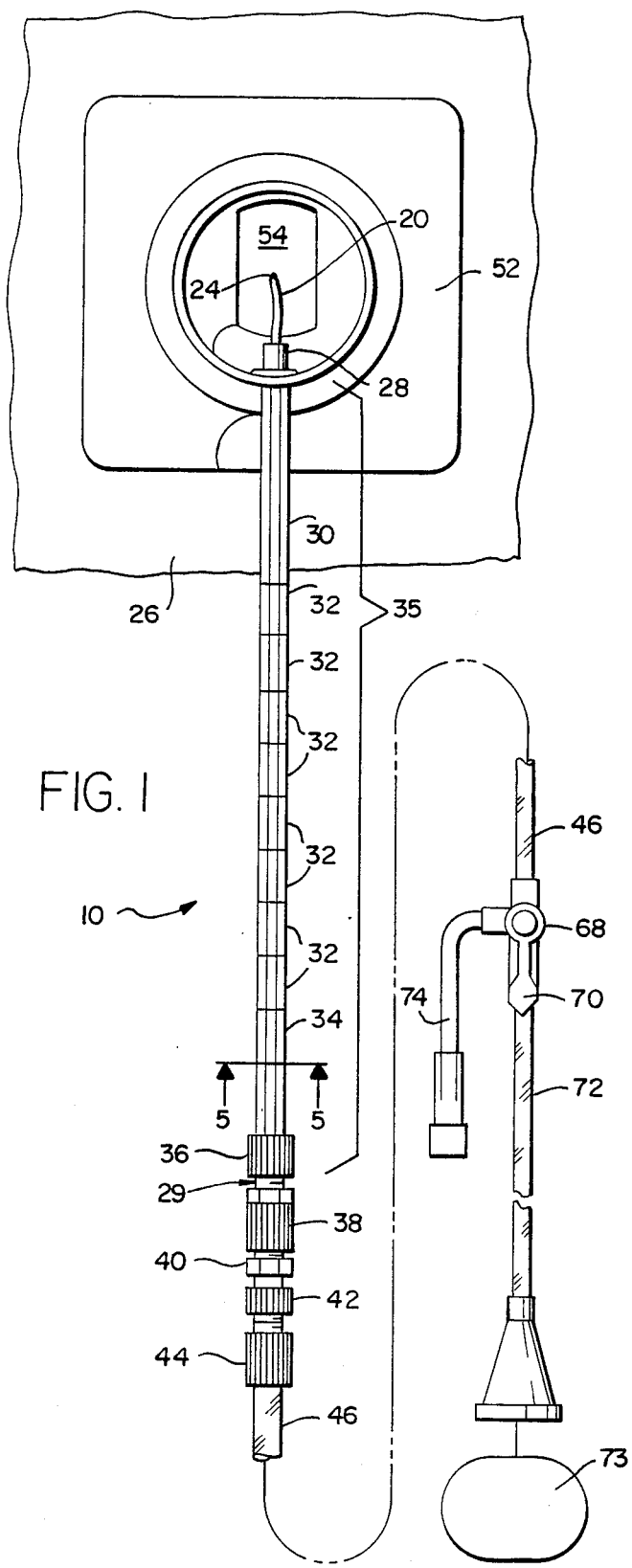
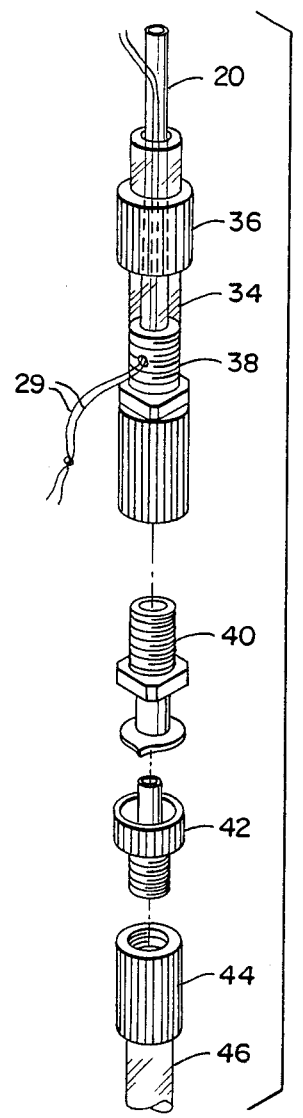

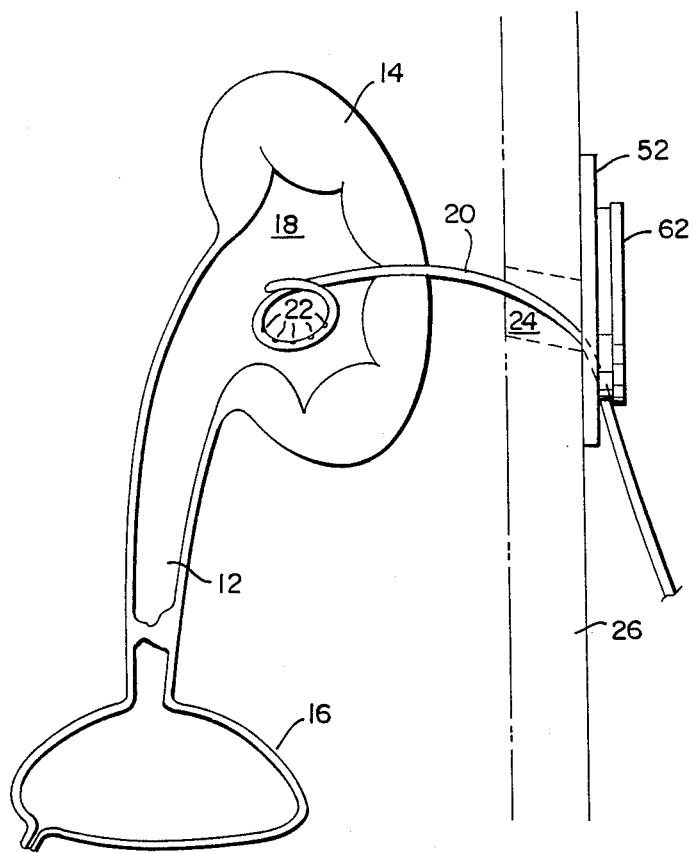
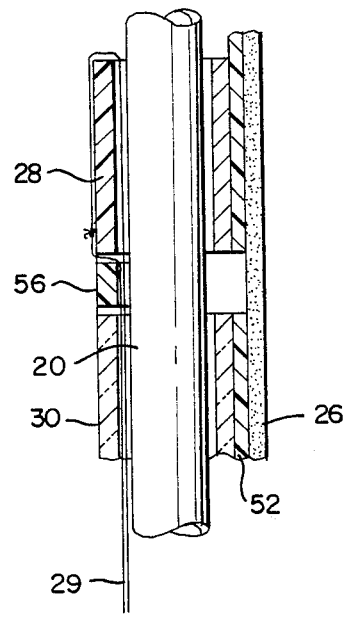
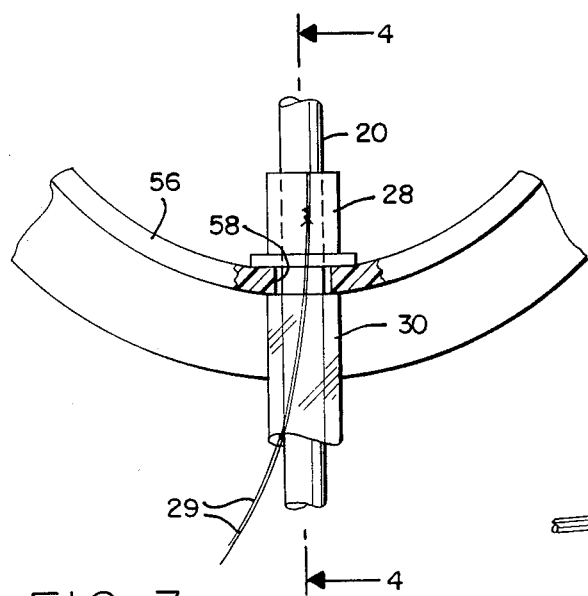
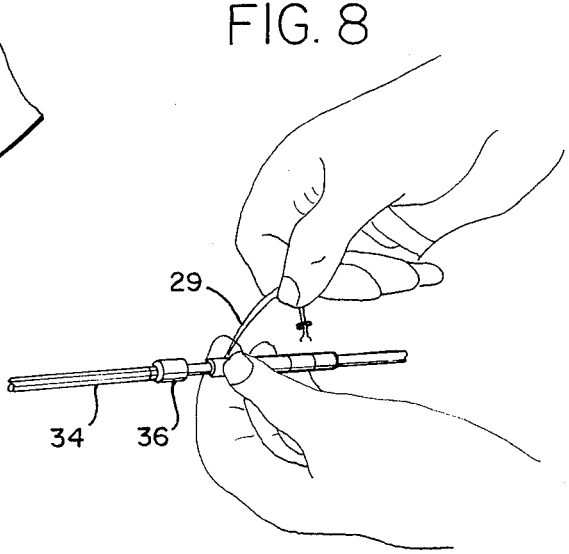
FIG. 2
FIG. 4
FIG. 3
FIG. 8

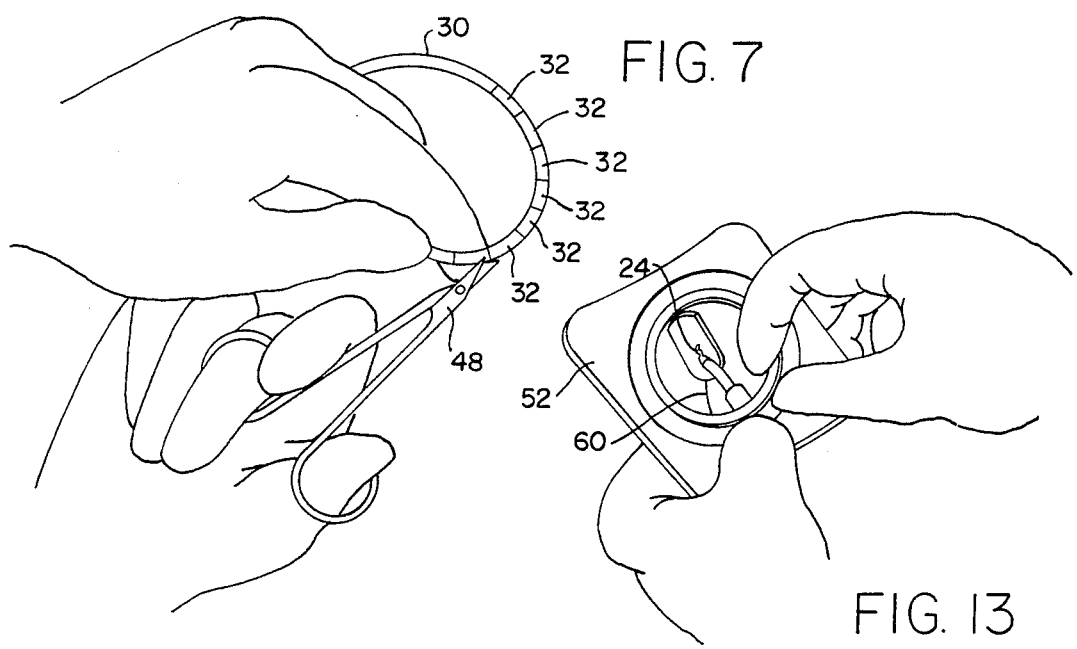
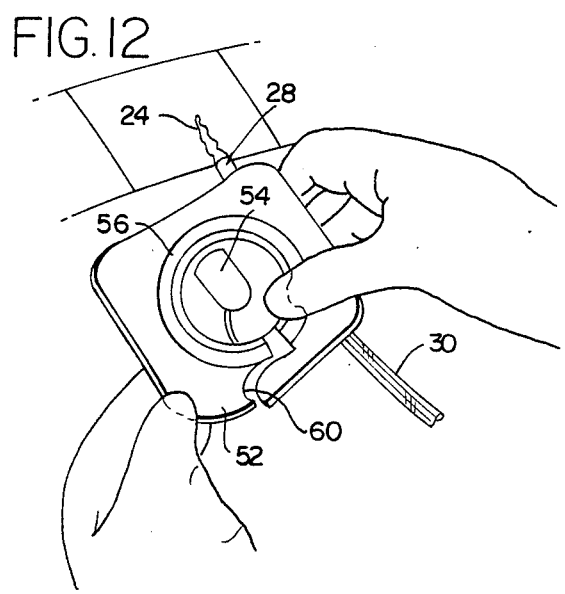
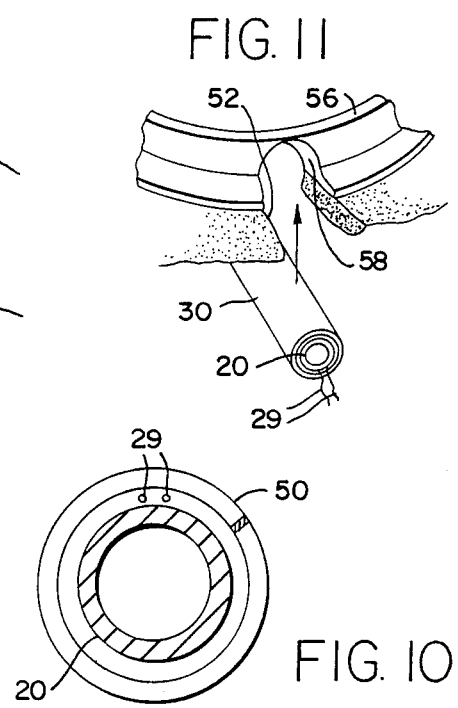
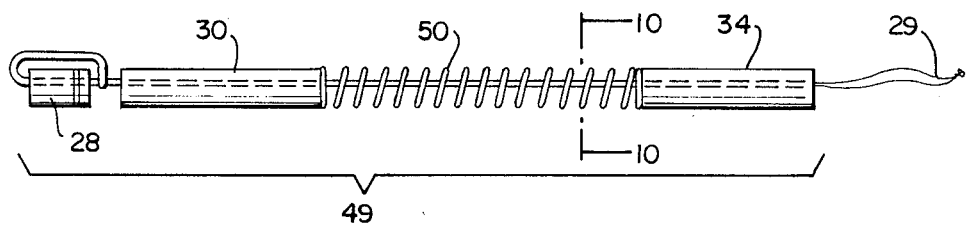

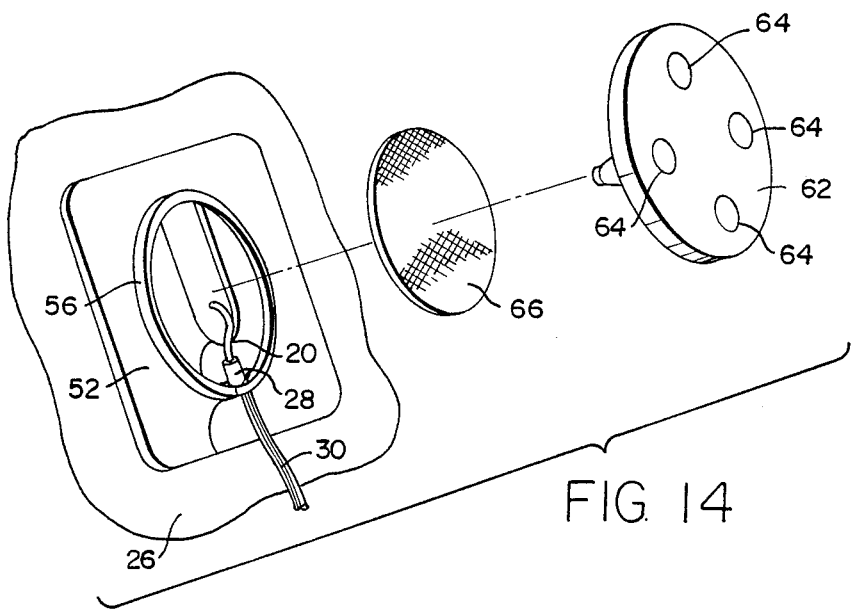
FIG. 14
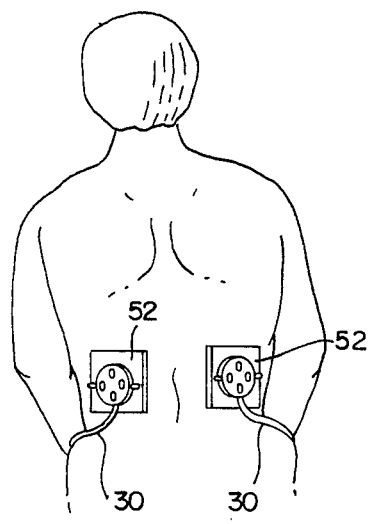
FIG. 15
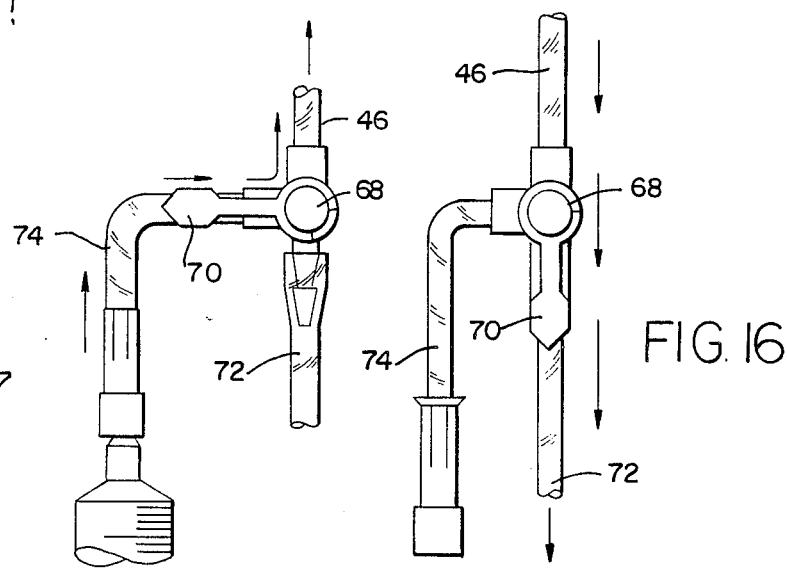
FIG. 17
FIG. 16

ANCHORING MECHANISM FOR AN ADJUSTABLE LENGTH PERCUTANEOUS DRAINAGE CATHETER

BACKGROUND OF THE INVENTION

This application is a continuation of Ser. No. 920,422 filed Oct. 20, 1986, now abandoned.

A. Field of the Invention

This invention relates to a catheter apparatus for draining or injecting fluids into a patient. In particular the invention relates to an apparatus for anchoring the catheter to the skin of a patient and for adjusting the length of the catheter tube in the patient so as to prevent an excessive length of tubing from being in the patient which can result in among other problems kinking of the tubing and thereby cause blockage of fluid flow. Alternatively there can be an insufficient length of tubing in the patient and thereby result in withdrawal of the catheter from an organ in the patient such as the kidney.

B. Description of the Prior Art

Use of catheters to drain fluids from or inject fluids into a patient is known and is a well accepted method in medical treatment. For example, patient's having the passage between a kidney and the bladder blocked have been treated by cathertization of the kidney to drain urine. The catheters which have been previously used are inserted into a patient using a needle. The distal end of the catheter includes multiple openings for passing fluid to or from the catheter tube. To facilitate retention of the catheter in an organ the distal end of catheters have been coiled in loops (e.g., see U.S. Pat. No. 4,419,094, entitled Suprapubic Catheter System, issued Dec. 6, 1983).

At the location where the catheter exits the patient's body catheters have been anchored to the skin with plastic plates held against the skin with adhesives (e.g., see again U.S. Pat. No. 4,419,094). Other previously known plastic plates for anchoring catheter tubes to a patient's skin have included radial slits from the outer edge of the plate to the location where the catheter tube passes through the plate. The slits are used to facilitate positioning of the catheter in the plate without having to thread the catheter through a hole in the plate. To hold the catheters to the plate clamps have been used. Additionally set screws to fix the position of catheter tubes have been used. These previously known plates for anchoring catheter tubes have also included chambers in which gauze is positioned about the catheter tubes at the locations where the tubes enter patient's bodies (e.g., see U.S. Pat. No. 4,516,968, entitled Catheter Shield and Method of Use, issued May 14, 1985).

SUMMARY OF THE INVENTION

This invention provides a catheter with a convenient and reliable apparatus for anchoring the catheter tube to a patient's skin along with a length adjusting mechanism to maintain the optimum length between the patient's organ where the catheter is inserted and the patient's skin where the catheter is anchored to the patient. The length adjusting mechanism is located on the catheter outside the patient so that it can be easily operated for adjusting the length of the catheter inside the patient.

The catheter of the invention can have a straight distal end or a looped distal end for positioning in a patient's organ so that the catheter is conveniently retained in the organ despite movements by the patient.

At the incision where the catheter exits from the patient the present invention includes an adhesive backed retaining plate having a chamber for packing gauze to surround the wound where the catheter enters the patient. Where the catheter passes through the retaining plate a bushing is mounted about the catheter. The bushing is dimensioned to be mounted against the retaining plate so that it will not move with respect to the retaining plate. The catheter however is dimensioned so the bushing can move along the catheter tube as the length adjusting mechanism is operated.

Attached to the bushing is one end of the length adjusting mechanism which is used to control the length of the catheter in the patient. By using the length adjustment mechanism the proper length of the catheter in the patient can be set. Thus excessive length which can cause kinking of the catheter is avoided, also the situation of having insufficient length is avoided.

BRIEF DESCRIPTION OF THE DRAWINGS

The novel features of the invention will be more readily appreciated from the following description when read in conjunction with the appended drawings, in which corresponding components are designated by the same reference numerals throughout the various figures.

FIG. 1 is an elevational view of the catheter apparatus of the present invention;

FIG. 2 is an enlarged schematic elevational view of a patient's kidney and bladder showing the extension from the kidney to the patient's skin of the catheter tube of the present invention, and also shows the retaining plate of the catheter tube adhered to the patient's skin;

FIG. 3 is an enlarged fragmentary elevational view, partially in section, of the retaining plate shown in FIGS. 1 and 2 and the members associated with the catheter tube;

FIG. 4 is an enlarged sectional view taken substantially on the line 4—4 of FIG. 3 and illustrates in additional detail the contruction of certain of the members shown in FIG. 3;

FIG. 5 is a sectional view substantially on the line 5—5 of FIG. 1 and illustrates in additional detail the construction and relative disposition of certain of the components shown in FIG. 1;

FIG. 6 is an enlarged exploded elevational view of certain of the components shown in FIG. 1;

FIG. 7 is a perspective view of a section of the catheter tube of the present invention as sleeve sections are being removed;

FIG. 8 is a perspective view of a section of the catheter tube of the present invention as the string of the associated length adjusting mechanism is being tightened;

FIG. 9 is a fragmentary sectional view of components for an alternative embodiment of a length adjusting mechanism;

FIG. 10 is a sectional view of the components shown in FIG. 9 as taken substantially on the line 10—10, FIG. 11 is a perspective view showing the positioning of the catheter tube with its length adjusting mechanism in an aperture located in an wall of the retaining plate;

FIGS. 12 and 13 are perspective views of the retaining plate of the present invention showing the positioning of the catheter tube with its first bushing in the retaining plate;

FIG. 14 is an enlarged exploded perspective view of the retaining plate;

FIG. 15 is a schematic view of the back of a patient showing attachment to the patient of the catheter apparatus included in this invention;

FIG. 16 is an enlarged fragmentary elevational view of a valve arrangement included in the components shown in FIG. 1 and illustrates the operation of the valve in a first mode; and, FIG. 17 is a view corresponding to that shown in FIG. 16 but illustrates the operation of the valve in a second mode.

DETAILED DESCRIPTION OF THE INVENTION

A catheter apparatus according to the present invention is shown in FIG. 1 where it is generally designated by reference numeral 10. As described below the catheter apparatus 10 of the present invention is used in conjunction with draining urine from a kidney. It is not intended however that the catheter apparatus 10 only be used to drain urine from a kidney. Instead this use was selected as being generally descriptive of the many types of medical treatments where the catheter apparatus 10 can be used when fluids are drained from or injected into a patient.

If the ureter 12 from a kidney 14 to the bladder 16 is blocked urine will accumulate in the hollow interior 18 of the kidney 14 (see FIG. 2). To drain the accumulated urine, the catheter apparatus 10 can be used with a catheter tube 20 inserted in the kidney 14 having the blocked ureter 12. The catheter tube 20 can be made of plastic as is known in the art. At the distal end of the catheter tube 20 multiple passages 22 into the catheter tube 20 are made to permit fluid to drain into or out of the catheter tube 20. The distal end of the catheter tube 20 can be stressed prior to insertion into the patient to provide a loop shape to facilitate retention in the hollow interior 18 of the kidney 14 of the catheter tube 20 (see FIG. 2). Insertion of the catheter tube 20 into a patient is through an incision 24 made in the skin 26 of the patient.

Prior to insertion of the catheter tube 20 into the patient a first bushing 28 having an interior hole diameter larger than the outer diameter of the catheter tube 20 is slid over the catheter tube 20 toward the distal end. Included with this bushing 28 is a string 29 looped through a hole in bushing 28 (see FIGS. 3 and 4). Next a hollow first sleeve 30, again having an inside diameter larger than the outside diameter of the catheter tube 20, is slid over catheter tube 20 and string 29 (see FIG. 5) against the bushing 28. This first sleeve 30 is approximately six centimeters long and can be made of plastic tubing. Additionally slid over the catheter tube 20 and string 29 are spacer sleeves 32. These spacer sleeves 32 can also be sections of plastic tubing and are approximately one to two centimeters in length. For convenience six to eight spacer sleeves 32 can be used. Finally a second sleeve 34 is slid over the catheter tube 20 and string 29 and positioned against the spacer sleeves 32. The second sleeve 34 can also be a section of plastic tubing which can be approximately four centimeters long.

At the proximal end of catheter tube 20 a female threaded bushing 36 is slid over catheter tube 20, second sleeve 34 and string 29 (see FIG. 6). Then abutted against the end of catheter tube 20 is a distal male threaded and proximal female threaded end bushing 38. In the male threaded section of end bushing 38 is a hole through which string 29 is passed (see FIG. 6). By pulling the string 29 tight, the first bushing 28 is pulled against first sleeve 30, and all of sleeve sections 32 and second sleeve 34 are held in a tight relationship. Then the female threaded bushing 36 can be threaded onto the the distal end of bushing 38 and over the string 29 to lock the string 29 in position. Threaded into the proximal end of bushing 38 is a male Luer lock piece 40. A female Luer lock piece 42 can be used with a female threaded end bushing 44 for connnecting a plastic tube 46 to the catheter tube 20 (see FIG. 6).

Using known techniques a physician can determine the distance from the patient's kidney 14 to the section of skin 26 where the incision 24 for inserting the catheter tube 20 is made. Knowing this distance the surgeon can use a pair of scissors 48 to cut and remove the necessary number of sleeve sections 32 so that the proper length of the catheter tube 20 is obtained (see FIG. 7). After the appropriate number of sleeve sections 32 have been removed the first threaded bushing 36 is loosened from the end bushing 38 and again string 29 is pulled tight and the first threaded bushing 36 is tightened onto the end bushing 38 to prevent the string 29 from moving (see FIG. 8).

An alternative catheter tube 20 length adjusting mechanism is illustrated in FIGS. 9 and 10. Here a spring 50 replaces the sleeve sections 32 of the embodiment shown in FIG. 1. The spring 50 now encloses the string 29 along its course with the catheter tube 20 between the first sleeve 30 and the second sleeve 34 (the catheter tube 20 is not shown in FIG. 9). In the embodiment shown in FIG. 9, no sleeve sections 32 have to be removed. The spring 50 can simply be compressed by exerting a pulling force on the string 29 as shown in FIG. 8 which results in pulling the bushing 28 toward the proximal end of catheter tube 20, thus exposing the proper length of catheter tube 20 for insertion into the patient.

The catheter tube 20 can be inserted into a kidney 14 in a manner well known in the art. For example, a needle (not shown) with a sheath (not shown) can be inserted into the hollow space 18 of the kidney 14 through an incision 24. The needle is then withdrawn but the sheath is retained in the position from the incision 24 to the hollow space 18 in the kidney 14. A flexible metal guide wire (not shown) is then inserted through the sheath. After the guide wire is passed through the sheath, the sheath is withdrawn, leaving the guide wire positioned from the incision 24 to the hollow space 18 in the kidney 14.

Tubings of progressively larger diameters are passed along the length of the guide wire to expand the diameter of the passage through the patient's body between the incision 24 and the hollow space 18 in the kidney 14. After each tube is passed over the guide wire, it is withdrawn before the next tube of increased diameter is passed over the guide wire. Finally the catheter tube 20 is passed into the hollow space 18 of the kidney 14 and the guide wire is removed from the patient. As positioned in the patient the catheter tube 20 has the first bushing 28 properly located for interconnection to a retaining plate 52 because of the prior use of a length adjusting mechanism (either 35 or 49, see FIGS. 1 and 9).

The retaining plate 52 is fabricated from plastic with an adhesive backing. A suitable wafer plastic plate with an adhesive backing is sold by Squibb under the trademark STOMAHESIVE. The retaining plate 52 includes a central cutout opening 54. The retaining plate 52 is adhered to the patient's skin 26 so that the incision 24 is essentially positioned in the middle of the cutout opening 54 (see FIG. 1). A wall 56 extends from the retaining plate 52 and away from the patient's skin 26. An aperture 58 is provided in the wall 56 so that the catheter tube 20 with either length adjusting mechanism 35 or 49 can be placed through the aperture 58 (see FIG. 11). The first bushing 28 is now positioned against the inside surface of the aperture 58 in the wall 56. The first sleeve 30 is positioned against the outside surface of the aperture 58 on the wall 56. The positioning of the catheter tube 20 with its first bushing 28 against the aperture 58 is faciliated by providing a cut 60 in the retaining plate 52. Specifically the cut 60 permits the threading of the catheter tube 20 through the aperture 58 and the positioning of the first bushing 28 against the aperture 58 by providing for enlargement of the aperture 58 as a result of separating the portions of the retaining plate 52 adjacent the cut 60. This may be seen in FIGS. 12 and 13.

A cover 62 is provided with openings 64 (see FIG. 14) for the opening above the wall 56 in the retaining plate 52. An absorbent material such as cotton gauze 66 may be placed within the wall 56 above the retaining plate 52 and held in place by the cover 62 which can be fixed to the wall 56 by a press fit. The cotton gauze 66 absorbs any fluid passing from the incision 24 and also serves to additionally retain the catheter tube 20 in a fixed position with respect to the retaining plate 52. The openings 64 in the cover 62 permit visual inspection of the cotton gauze 66 so that it can be replaced when necessary. The openings 64 also provide for areation of the incision 24.

The use of two catheter apparatus 10 of the present invention in a patient is generally shown in FIG. 15.

After the catheter apparatus 10 is positioned in a patient the tube 46 (see FIGS. 1, 16 and 17) can be connected to a two way valve 68 having a handle 70. In one position of the handle 70 (see FIG. 16), the tube 46 is connected for fluid flow only through tube 72 which empties into a urine collection pouch 73 (see FIG. 1). This is indicated by arrows in FIG. 16. In a second position of the handle 70 (see FIG. 17), the tube 46 is connected for fluid flow only through tube 74. This is indicated by arrows in FIG. 17. Then tube 74 can be used for injection into the kidney 14 of a fluid such as medicine or a testing material.

The above discusion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A catheter device comprising:
    a tube having a distal portion for insertion into the body of a patient,
    retaining means for attaching said device to the skin of a patient,
    an aperture in said retaining means defining a passage for said tube,
    a perimeter wall attached to said retaining means, and
    adjusting means for controlling the length of said tube available for insertion into a patient's body without applying pressure to the external surface of said tube, said adjusting means comprising:
        first retention means adjacent the proximal end of said tube,
        second retention means slidably mounted on said tube and spaced distally from said first retention means, and
        means for sliding said second retention means toward said first retention means to provide a distal portion of said tube of appropriate length for insertion into a patient's body.

2. A catheter device as defined by claim 1 in which said adjusting means further comprises means for varying the length of said tube over which said second retention means may be slid toward said first retention means.

3. A catheter device as defined by claim 2 in which said means for sliding said second retention means is a string positioned outside of said tube.

4. A catheter device as defined by claim 1 in which said wall includes an aperture defining a passage for said tube.

5. A catheter device as defined by claim 4 in which said second retaining means is dimensioned to be fixedly fit into said aperture in said wall.

6. A catheter device as defined by claim 1 in which said wall defines a chamber above said retaining means.

7. A catheter device as defined by claim 6 further comprising cover means for said chamber said cover means being removable without disturbing said retention means.

8. A catheter device as defined by claim 7 in which said cover means is apertured.

9. A catheter device as defined by claim 1 further comprising fluid flow control means on a proximal portion of said tube.

10. A catheter device as defined by claim 9 in which said fluid flow control means is a valve.

11. A catheter device comprising:
    a tube having a distal portion for insertion into the body of a patient,
    retaining means for attaching said device to the skin of a patient,
    an aperture in said retaining means defining a passage for said tube,
    a perimeter wall attached to said retaining means, and
    adjusting means for controlling the length of said tube available for insertion into a patient's body, said adjusting means comprising:
        first retention means adjacent the proximal end of said tube,
        second retention means slidably mounted on said tube and spaced distally from said first retention means, and
        means for sliding said second retention means toward said first retention means to provide a distal portion of said tube of appropriate length for insertion into a patient's body; and
    spring means for varying the length of said tube over which said second retention means may be slid toward said first retention means.

12. A catheter device comprising:
    a tube having a distal portion for insertion into the body of a patient,
    retaining means for attaching said device to the skin of a patient, an aperture in said retaining means defining a passage for said tube, a perimeter wall attached to said retaining means, and adjusting means for controlling the length of said tube available for insertion into a patient's body, said adjusting means comprising:

first retention means adjacent the proximal end of said tube, second retention means slidably mounted on said tube and spaced distally from said first retention means, and means for sliding said second retention means toward said first retention means to provide a distal portion of said tube of appropriate length for insertion into a patient's body; and a sleeve having removable sections disposed about said tube for varying the length of said tube over which said second retention means may be slid toward said first retention means.

13. A catheter device as defined by claim 11 or 12 in which said means for sliding said second retention means is a string positioned outside of said tube.

* * * * *